United States Patent

Riebel et al.

[11] Patent Number: 5,217,522
[45] Date of Patent: Jun. 8, 1993

[54] HERBICIDAL SULPHONYLGUANIDINOAZINES

[75] Inventors: Hans-Jochem Riebel; Christa Fest, both of Wuppertal; Ernst R. F. Gesing, Erkrath-Hochdahl; Rolf Kirsten, Monheim; Joachim Kluth, Langenfeld; Klaus-Helmut Müller, Düsseldorf; Klaus Lürssen, Bergisch Gladbach; Hans-Joachim Santel, Leverkusen; Robert E. Schmidt, Bergisch Gladbach, all of Fed. Rep. of Germany

[73] Assignee: Bayer Aktiengesellschaft, Leverkusen, Fed. Rep. of Germany

[21] Appl. No.: 858,903

[22] Filed: Mar. 27, 1992

[30] Foreign Application Priority Data

Apr. 4, 1991 [DE] Fed. Rep. of Germany ....... 4110882

[51] Int. Cl.$^5$ .................. C07D 239/69; A01N 43/54
[52] U.S. Cl. .................. 504/239; 544/321; 544/323; 544/332; 504/232; 504/242; 504/243; 504/230; 504/232; 504/234; 504/168
[58] Field of Search ............ 71/92, 90; 544/321, 544/323, 332

[56] References Cited

U.S. PATENT DOCUMENTS 4,602,938 7/1986 Moriya et al. .................. 71/90
4,725,303 2/1988 Moriya et al. .................. 71/92
5,092,917 3/1992 Fest et al. .................. 71/92

FOREIGN PATENT DOCUMENTS 0173319  3/1986  European Pat. Off. .
0343462 11/1989 European Pat. Off. .
0414067  2/1991  European Pat. Off. .
0431270  6/1991  European Pat. Off. .

*Primary Examiner*—John M. Ford
*Attorney, Agent, or Firm*—Sprung Horn Kramer & Woods

[57] ABSTRACT

Herbicidal sulphonylguanidinoazines of the formula

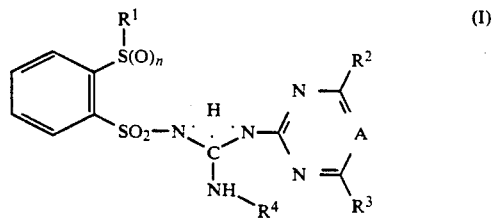

in which
n represents the numbers 1 or 2,
A represents nitrogen or a C-X group, where X represents hydrogen or halogen.

4 Claims, No Drawings

HERBICIDAL SULPHONYLGUANIDINOAZINES

The invention relates to new sulphonylguanidinoazines, processes for their preparation and their use as herbicides.

It is known that certain sulphonylguanidinoazines such as, for example, N'-(4,6-dimethyl-pyrimidin-2-yl)-N''-amino-N'''-(2-diethylaminosulphonyl-phenylsulphonyl)guanidine, have herbicidal properties (cf. EP-A 173,319; cf. also EP-A 121,082, EP-A 343,462 and U.S. Pat. No. 4,725,303). However, the herbicidal action of the sulphonylguanidinoazines known hitherto is not always entirely satisfactory.

Substituted sulphonylamidinohydrazones are the subject of earlier, but not previously published patent applications (cf. DE Patent 3,933,792/LeA 27241 of 10.10.1989 and DE Patent 4,017,460/LeA 27629 of 31.05.1990).

New sulphonylguanidinoazines of the general formula (I)

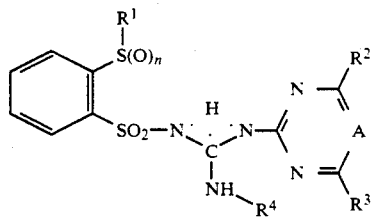

in which
n represents the numbers 1 or 2,
A represents nitrogen or a C-X group, where X represents hydrogen or halogen,
$R^1$ represents alkyl having at least two carbon atoms,
$R^2$ and $R^3$ are identical or different and represent hydrogen, halogen, alkyl, halogenoalkyl, alkoxyalkyl, alkoxy, halogenoalkoxy, alkylthio, alkylamino or dialkylamino, and
$R^4$ represents amino or the group

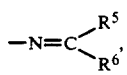

in which
$R^5$ represents hydrogen or alkyl, aryl or aralkyl which are in each case optionally substituted,
$R^6$ represents hydrogen or alkyl, alkenyl, alkadienyl, alkinyl, (hetero)aryl, aralkyl, aralkenyl, alkoxy, alkoxycarbonyl or dialkylamino which are in each case optionally substituted, or together with $R^5$ represents optionally substituted alkanediyl,
have now been found.

The general formula (I) represents the individual possible tautomers of the formulae (IA), (IB) and (IC)

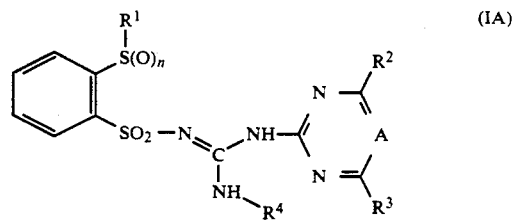

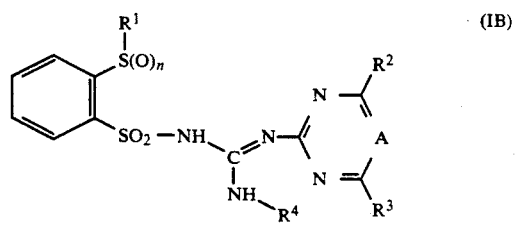

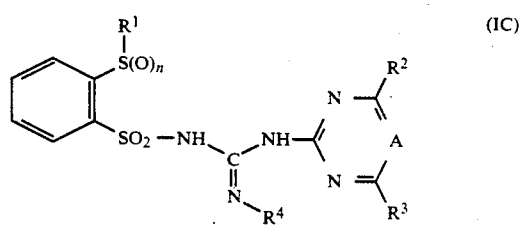

and the mixtures of these tautomers and also the E- and Z-isomers which are due to the C-N-double bonds present in each case, and their mixtures.

The new sulphonylquanidinoazines of the general formula (I) are obtained when (a) in the case in which $R^4$ represents amino and n, A, $R^1$, $R^2$ and $R^3$ have the abovementioned meanings, sulphonyliso(thio)ureas of the general formula (II)

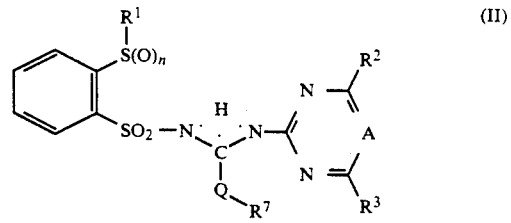

in which
n, A, $R^1$, $R^2$ and $R^3$ have the abovementioned meanings,
Q represents oxygen or sulphur and
$R^7$ represents alkyl, aralkyl or aryl which are optionally substituted in each case,
are reacted with hydrazines or a hydrazine-water or hydrazine-acid adduct,
if appropriate in the presence of an acid acceptor and if appropriate in the presence of a diluent, or when (b) in the case in which $R^4$ represents the group

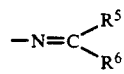

and n, A, $R^1$, $R^2$, $R^3$, $R^5$ and $R^6$ have the abovementioned meanings, sulphonylguanidinoazines of the general formula (I) in which $R^4$ represents amino and n, A, $R^1$, $R^2$ and $R^3$ have the abovementioned meanings, are reacted with carbonyl compounds of the general formula (III)

$$R^5-\overset{O}{\underset{\|}{C}}-R^6 \qquad (III)$$

in which $R^5$ and $R^6$ have the abovementioned meanings, or with N,N-dialkyl-carboxamide acetals or ketals if appropriate in the presence of a condensation auxiliary and if appropriate in the presence of a diluent.

The new sulphonylguanidinoazines of the formula I are distinguished by strong herbicidal activity.

Surprisingly, the new sulphonylguanidinoazines of the general formula (I) show considerably stronger herbicidal action than previously known compounds of a similar structure and a similar type of action, such as, for example, N'-(4,6-dimethyl-pyrimidin-2-yl)-N''-amino-N'''-(2-diethylaminosulphonyl-phenylsulphonyl)-guanidine (cf. EP-A 173,319).

The invention preferably relates to new sulphonylguanidinoazines of the formula (I), in which n represents the numbers 1 or 2, A represents nitrogen or a C-X group, where X represents hydrogen, fluorine or chlorine, $R^1$ represents $C_2$-$C_6$-alkyl, $R^2$ and $R^3$ are identical or different and represent hydrogen, fluorine, chlorine, bromine, $C_1$-$C_4$-alkyl, $C_1$-$C_4$-halogenoalkyl, $C_1$-$C_2$-alkoxy-$C_1$-$C_2$-alkyl, $C_1$-$C_4$-alkoxy, $C_1$-$C_4$-halogenoalkoxy, $C_1$-$C_4$-alkylthio, $C_1$-$C_4$-alkylamino or di-($C_1$-$C_2$-alkyl)amino, and $R^4$ represents amino or the group $$-N=C\begin{matrix}R^5\\R^6\end{matrix},$$

in which $R^5$ represents hydrogen, $C_1$-$C_6$-alkyl which is optionally substituted by fluorine, chlorine and/or bromine, or phenyl or benzyl which are in each case optionally substituted by fluorine, chlorine, bromine, $C_1$-$C_4$ alkyl and/or $C_1$-$C_4$-alkoxy, $R^6$ represents hydrogen, $C_1$-$C_{20}$-alkyl, $C_2$-$C_{10}$-alkenyl, $C_2$-$C_{10}$-alkinyl or $C_4$-$C_{10}$-alkadienyl which are in each case optionally substituted by fluorine, chlorine and/or bromine, $C_1$-$C_4$-alkoxy-$C_1$-$C_4$-alkyl, $C_1$-$C_4$-alkylthio-$C_1$-$C_4$-alkyl, phenyl which is optionally substituted by fluorine, chlorine, bromine, carboxyl, cyano, nitro, amino, $C_1$-$C_4$-alkyl (which is optionally substituted by fluorine and/or chlorine), $C_1$-$C_4$-alkoxy (which is optionally substituted by fluorine and/or chlorine), $C_1$-$C_4$-alkylthio (which is optionally substituted by fluorine and/or chlorine), di-($C_1$-$C_4$-alkyl)-amino, $C_1$-$C_4$-alkoxy-carbonyl and/or phenoxy (which is optionally substituted by fluorine, chlorine and/or trifluoromethyl), or naphthyl, or represents pyridyl, pyrrolyl, furyl, thiazolyl or thienyl which are in each case optionally substituted by cyano, nitro, fluorine, chlorine, bromine, $C_1$-$C_4$-alkyl and/or $C_1$-$C_4$-alkoxy, or represents dithienyl, or phenyl-$C_1$-$C_2$-alkyl or phenylethenyl which are in each case optionally substituted by fluorine, chlorine, bromine, $C_1$-$C_4$-alkyl and/or $C_1$-$C_6$-alkoxy, or represents $C_1$-$C_6$-alkoxy, $C_1$-$C_6$-alkoxy-carbonyl or di-($C_1$-$C_4$-alkyl)amino, or together with $R^5$ represents $C_2$-$C_6$-alkanediyl which is optionally substituted by fluorine, chlorine, bromine, $C_1$-$C_4$-alkyl and/or $C_1$-$C_4$-alkoxycarbonyl.

The invention relates in particular to compounds of the formula (I), in which n represents the numbers 1 or 2, A represents nitrogen or a CH group, $R^1$ represents ethyl, propyl, isopropyl, butyl, isobutyl or sec-butyl, $R^2$ represents hydrogen, chlorine, methyl, ethyl, trifluoromethyl, methoxymethyl, methoxy, ethoxy, difluoromethoxy, methylthio, methylamino, ethylamino or dimethylamino, $R^3$ represents hydrogen, chlorine, methyl, ethyl, trifluoromethyl, methoxy, ethoxy, difluoromethoxy, methylthio, methylamino, ethylamino or dimethylamino, and $R^4$ represents amino or the group $$-N=C\begin{matrix}R^5\\R^6\end{matrix},$$

in which $R^5$ represents hydrogen, $C_1$-$C_4$-alkyl or phenyl, $R^6$ represents $C_1$-$C_{10}$-alkyl, $C_2$-$C_{10}$-alkenyl or $C_4$-$C_{10}$-alkadienyl, phenyl which is optionally substituted by fluorine, chlorine, bromine, carboxyl, cyano, nitro, methyl, ethyl, trifluoromethyl, methoxy, ethoxy, difluoromethoxy, trifluoromethoxy, methylthio, ethylthio, difluoromethylthio, trifluoromethylthio, dimethylamino and/or phenoxy (which is optionally substituted by fluorine, chlorine and/or trifluoromethyl), pyridyl, furyl, thiazolyl or thienyl which are in each case optionally substituted by cyano, nitro, fluorine, chlorine, bromine, methyl, ethyl. methoxy or ethoxy, or represents dithienyl, benzyl or phenylethenyl, $C_1$-$C_4$-alkoxy, $C_1$-$C_4$-alkoxycarbonyl or dimethylamino, or together with $R^5$ represents butane-1,4-diyl (tetramethylene) or pentane-1,5-diyl (pentamethylene).

If, for example, N'-(4,6-dimethoxy-s-triazin-2-yl)-N''-(2-propylsulphonyl-phenylsulphonyl)-S-methyl-isothiourea and hydrazine are used as starting substances, the course of the reaction in process (a) according to the invention can be outlined by the following equation:

[Chemical structure diagram showing reaction with $N_2H_4$ / $-HSCH_3$]

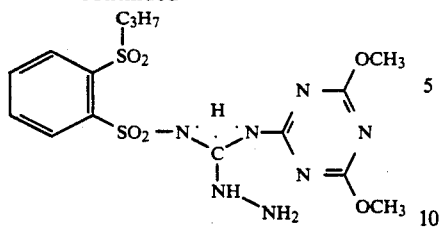

If, for example, N'-(4,6-dimethoxy-pyrimidin-2-yl)-N''-amino-N'''-(2-ethylsulphinyl-phenylsulphonyl)-quanidine and acetone are used as starting substances, the course of the reaction in process (b) according to the invention can be outlined by the following equation:

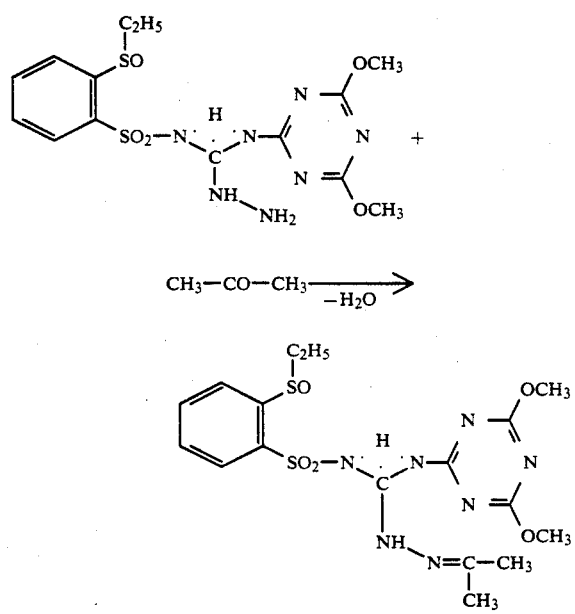

Formula (II) provides a general definition of the sulphonyliso(thio)ureas to be used as starting substances for the preparation of compounds of the formula (I) in process (a) according to the invention.

In formula (II) n, A, $R^1$, $R^2$ and $R^3$ preferably or in particular have those meanings which have already been indicated above as preferred or as particularly preferred for n, A, $R^1$, $R^2$ and $R^3$ in connection with the description of the compounds of the formula (I) according to the invention;

Q preferably represents oxygen or sulphur and
$R^7$ preferably represents $C_1$-$C_4$-alkyl which is optionally substituted by carboxyl, $C_1$-$C_4$-alkoxycarbonyl or $C_1$-$C_4$-alkoxy, in particular methyl, or represents benzyl or phenyl which are in each case optionally substituted by fluorine, chlorine, bromine, $C_1$-$C_4$-alkyl or $C_1$-$C_4$-alkoxy.

The starting substances of the formula (II) are still unknown from the literature and are the subject of a patent application submitted in parallel.

The sulphonyliso(thio)ureas of the formula (II) are obtained when corresponding compounds of the general formula (IV)

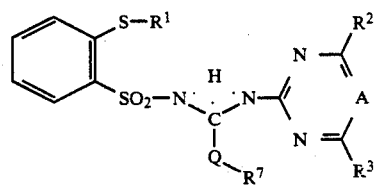

in which
n, A, $R^1$, $R^2$, $R^3$, Q and $R^7$ have the abovementioned meanings, are reacted with an oxidising agent, such as, for example, hydrogen peroxide, if appropriate in the presence of a diluent, such as, for example, acetic acid, at temperatures between 0° C. and 100° C..

The compounds of the formula (IV) are known and/or can be prepared by processes known per se (cf. EP-A 413,221).

Process (a) according to the invention is carried out using hydrazine or a hydrazine-water or hydrazine-acid adduct.

Suitable compounds are virtually anhydrous hydrazine or hydrazine hydrate and also hydrazine adducts with mineral acids, such as, for example, hydrazine mono- or dihydrochloride and hydrazine sulphate.

These compounds are known chemicals for synthesis.

Process (a) according to the invention for the preparation of the new sulphonylguanidinoazines of the formula (I) is preferably carried out using diluents. Suitable diluents here are preferably water and/or polar organic solvents, such as methanol, ethanol, isopropanol, butanol, isobutanol, sec-butanol, tert-butanol, glycol dimethyl ether, diglycol dimethyl ether, tetrahydrofuran, dioxane, methyl acetate, ethyl acetate, acetonitrile, propionitrile, dimethylformamide, dimethylacetamide, N-methylpyrrolidone, methylene chloride, chloroform, dimethyl sulphoxide and tetramethylene sulphone.

Acid acceptors which can be employed in the process according to the invention are all acid-binding agents which can customarily be used for reactions of this type. Those which are preferred are alkali metal hydroxides such as, for example, sodium hydroxide and potassium hydroxide, alkaline earth metal hydroxides such as, for example, calcium hydroxide, alkali metal carbonates and alkoxides such as sodium carbonate and potassium carbonate, sodium tert-butoxide and potassium tert-butoxide, furthermore aliphatic, aromatic or heterocyclic amines, for example triethylamine, trimethylamine, dimethylaniline, dimethylbenzylamine, pyridine, 1,5-diazabicyclo4.3.0]-non-5-ene (DBN), 1,8-diazabicyclo-[5.4.0]-undec-7-ene (DBU) and 1,4-diazabicyclo-[2.2.2]-octane (DABCO).

The reaction temperatures can be varied within a substantial range in process (a) according to the invention. In general, the reaction is carried out at temperatures between −20° C. and +80° C., preferably at temperatures between 0° C. and 50° C.

Process (a) according to the invention is in general carried out at normal pressure.

To carry out process (a) according to the invention, between 1 and 3 mol, preferably between 1.0 and 1.5 mol, of hydrazine or hydrazine-water adduct or hydrazine-acid adduct are in general employed per mole of sulphonyliso(thio)urea of the formula (II).

In general, the reaction components are mixed together at room temperature or with ice-cooling and the reaction mixture is stirred, if appropriate at elevated temperature, until the reaction is complete. The products are in general obtained in crystalline form; otherwise they can be obtained in crystalline form by concentration and trituration with a suitable diluent, such as, for example, ethanol and isolated by filtering off with suction.

Formula (I) provides a general definition of the compounds to be used as starting substances in process (b) according to the invention with the proviso that $R^4$ represents amino.

In this case, n, A, $R^1$, $R^2$ and $R^3$ preferably or in particular have those meanings which have already been indicated above as preferred or as particularly preferred in the context of the description of the compounds of the formula (I) according to the invention.

The starting substances of the formula (I) for process (b) which are described above are new compounds according to the invention; they can be prepared by process (a) according to the invention.

Formula (III) provides a general definition of the carbonyl compounds additionally to be used as starting substances for the preparation of compounds of the formula (I) in process (b) according to the invention.

In formula (III), $R^5$ and $R^6$ preferably or in particular have those meanings which have already been indicated above as preferred or as particularly preferred in connection with the description of the compounds of the formula (I) according to the invention.

Examples of the starting substances of the formula (III) which may be mentioned are:

formaldehyde, acetaldehyde, propionaldehyde, butyraldehyde, isobutyraldehyde, valeraldehyde, isovaleraldehyde, benzaldehyde, pyridine-4-, -2- and -3-carbaldehyde, furan-2- and -3-carbaldehyde and thiophene-2- and -3-carbaldehyde, furthermore also acetone, methyl ethyl ketone, methyl propyl ketone, methyl isopropyl ketone, methyl butyl ketone, methyl isobutyl ketone, diethyl ketone, acetophenone, benzophenone, cyclopentanone, cyclohexanone, phenylacetone, chloroacetone, chloral, methyl and ethyl glyoxylates, methyl and ethyl pyruvates, phthalaldehydic acid and 6-chloropyridine-3-aldehyde.

N,N-Dialkyl-carboxamide acetals or ketals which can additionally be employed as starting substances in process (b) according to the invention are preferably N,N-dialkyl-formamide or -acetamide acetals or ketals having straight-chain or branched alkyl radicals having 1 to 4 carbon atoms and bonded to N- or 0, such as, for example, N,N-dimethyl- and N,N-diethyl-formamide and -acetamide dimethyl acetal, diethyl acetal, dipropyl acetal, diisopropyl acetal, dibutyl acetal, diisobutyl acetal, di-sec-butyl acetal and di-tert-butyl acetal.

The starting substances of the formula (III) are known chemicals for organic synthesis.

Process (b) according to the invention for the preparation of the new compounds of the formula (I) is optionally carried out using diluents. Possible diluents here are virtually all the inert organic solvents. These preferably include aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, alcohols such as methanol, ethanol, propanol, isopropanol, butanol and isobutanol, esters such as methyl acetate and ethyl acetate, nitriles such as, for example, acetonitrile and propionitrile, amides such as, for example, dimethylformamide, dimethylacetamide and N-methyl-pyrrolidone and also dimethyl sulphoxide, tetramethylene sulphone and hexamethylphosphoric triamide.

Process (b) according to the invention is optionally carried out in the presence of a condensation auxiliary. Those which are suitable are preferably the drying agents which are customary in organic chemistry. These preferably include anhydrous salts, such as, for example, sodium sulphate, magnesium sulphate and potassium carbonate.

The reaction temperatures can be varied within a substantial range in process (b) according to the invention. In general, the reaction is carried out at temperatures between 0° C. and 100° C., preferably at temperatures between 10° C. and 80° C.

Process (b) according to the invention is in general carried out under normal pressure. However, it is also possible to work at elevated or reduced pressure.

To carry out process (b) according to the invention, between 1 and 1,000 mol, preferably between 1 and 500 mol, of a carbonyl compound of the formula (III) are in general employed relative to 1 mol of starting compound of the formula (I).

The reaction components are in general mixed at room temperature or with slight cooling and if appropriate stirred at elevated temperature until the reaction is complete. Working-up is carried out by customary methods (cf. the preparation examples).

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera; Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the cenera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pasture land and for the selective combating of weeds in annual cultures.

The compounds of the formula (I) according to the invention are particularly suitable for the selective control of monocotyledon and dicotyledon weeds in monocotyledon and dicotyledon cultures both in the pre-emergence and in the post-emergence method.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is, liquid solvents and/or solid carriers, optionally with the use of surface-active agents, that is, emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural minerals such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinylalcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For controlling weeds, the active compounds according to the invention, as such or in the form of their formulations, can also be used as mixtures with known herbicides, finished formulations or tank mixes being possible.

Suitable herbicides for the mixtures are known herbicides, such as, for example, 1-amino-6-ethylthio-3-(2,2-dimethylpropyl)-1,3,5-triazine-2,4(1H,3H)-dione (AMETHYDIONE) or N-(2-benzothiazolyl)-N,N'-dimethylurea (METABENZTHIAZURON) for combating weeds in cereals; 4-amino-3-methyl-6-phenyl-1,2,4-triazin-5(4H)-one (METAMITRON) for combating weeds in sugar beet and 4-amino-6-(1,1-dimethylethyl)-3-methylthio-1,2,4-triazin(5(4H)-one (METRIBUZIN) for combating weeds in soya beans; furthermore also 2,4-dichlorophenoxyacetic acid (2,4-D); 4-(2,4-dichlorophenoxy)-butyric acid (2,4-DB); 2,4-dichlorophenoxypropionic acid (2,4-DP); 2-chloro- o 2',6'-diethyl-N-methoxy-methylacetanilide (ALACHLOR); methyl-6,6-dimethyl-2,4-dioxo-3-[1-(2-propenyloxyamino)butylidene]-cyclohexanecarboxylic acid (ALLOXYDIM); 4-amino-benzenesulphonyl-methylcarbamate (ASULAM); 2-chloro-4-ethylamino-6-isopropylamino-1,3,5-triazine (ATRAZINE); methyl 2-[[[[(4,6-dimethoxypyrimidin-2-yl)amino]-carbonyl]-amino]-sulphonyl]-methyl]-benzoate (BENSULFURON); 3-isopropyl-2,1,3-benzothiadiazin-4-one 2,2-dioxide (BENTAZONE); methyl 5-(2,4-dichloro-phenoxy)-2-nitrobenzoate (BIFENOX); 3,5-dibromo-4-hydroxy-benzonitrile; (BROMOXYNIL); N-(butoxymethyl)-2-chloro-N-(2,6-diethylphenyl)-acetamide (BUTACHLOR); ethyl 2-{[(4-chloro-6-methoxy-2-pyrimidinyl)-aminocarbonyl]-aminosulphonyl}-benzoate (CHLORIMURON); N-(3-chlorophenyl)isopropyl-carbamate (CHLORPROPHAM); 2-chloro-N-{[(4-methoxy-6-methyl-1,3,5-triazin-2-yl)-amino]-carbonyl)-benzenesulphonamide (CHLORSULFURON); N,N-dimethyl-N'-(3-chloro-4-methylphenyl)-urea(CHLORTOLURON);exo-1-methyl-4-(1-methylethyl)-2-(2-methylphenyl-methoxy)-7-oxabicyclo-(2,2,1)-heptane (CINMETHYLIN); 3,6-dichloro-2pyridinecarboxylic acid (CLOPYRALID); 2-chloro-4-ethylamino-6-(3-cyanopropylamino)-1,3,5-triazine (CYANAZINE); N,S-diethyl N-cyclohexyl-thiocarbamate (CYCLOATE); 2-[1(ethoximino) -butyl]-3-hydroxy-5-[tetrahydro-(2H)-thiopyran-3-yl]-2-cyclohexen-1-one (CYCLOXYDIM); 2-[4-(2,4-dichlorophenoxy)-phenoxy]-propionic acid, its methyl ester or its ethyl ester (DICLOFOP); 2-[(2-chlorophenyl)methyl]-4,4-dimethylisoxazolidin-3-one (DIMETHAZONE); S-ethyl N,N-di-n-propyl-thiocarbamate (EPTAME); 4-amino-6-t-butyl-3-ethylthio-1,2,4-triazin-5(4H)-one (ETHIOZIN); 2-{4-[(6-chloro-2-benzoxazolyl)-oxy]-phenoxy}-propanoic acid, its methyl ester or its ethyl ester (FENOXAPROP); 2-[4-(5-trifluoromethyl-2-pyridyloxy)-phenoxy]-propanoic acid or its butyl ester (FLUAZIFOP); N,N-dimethyl-N'-(3-trifluoromethylphenyl)-urea (FLUOMETURON); 1-methyl-3-phenyl-5-(3-trifluoromethylphenyl)-4-pyridone (FLURIDONE); [(4-amino-3,5-dichloro-6-fluoro-2-pyridinyl)-oxy]acetic acid or its 1-methylheptyl ester (FLUROXYPYR); 2{4-[(3-chloro-5-(trifluoromethyl)-2-pyridinyl)-oxy]phenoxy}-propanoic acid or its ethyl ester (HALOXYFOP); 3-cyclohexyl-6-dimethylamino-1-methyl-1,3,5-triazin-2,4-dione (HEXAZINONE); methyl-2-[4,5-dihydro-4-methyl-4-(1- methylethyl)-5-oxo-1H-imidazol-2-yl]-4(5)-methylbenzoate (IMAZAMETHABENZ); 2-[5-methyl-5-(1-methylethyl)-4-oxo-2-imidazolin-2-yl]-3-quinolinecarboxylic acid (IMAZAQUIN); 2-[4,5-dihydro-4-methyl-4-isopropyl-5-oxo-(1H)-imidazol-2-yl]-5-ethyl-pyridine-3-carboxylic acid (IMAZETHAPYR); 3,5-diiodo-4-hydroxybenzonitrile(IOXYNIL);N,N-dimethyl-N'-(4-isopropylphenyl)-urea (ISOPROTURON); (2-methyl-4-chlorophenoxy)-acetic acid (MCPA); (4-chloro-2-methylphenoxy)-propionic acid (MCPP); N-methyl-2-(1,3-benzothiazol-2-yloxy)-acetanilide (MEFENACET); 2-chloro-N-(2,6-dimethylphenyl)-N-[(1H)-pyrazol-1-yl-methyl]-acetamide (METAZACHLOR); 2-ethyl-6-methyl-N-(1-methyl-2-methoxyethyl) -chloroacetanilide (METOLACHLOR); 2-{[[((4-methoxy-6-methyl-1,3,5-triazin-2-yl)-amino)-carbonyl]-amino]-sulphonyl}-benzoic acid or its methyl ester (METSULFURON); S-ethyl-N,N-hexamethylene-thiocarbamate (MOLINATE); 1-(3-trifluoromethyl-phenyl)-4-methylamino-5-chloro-6-pyridazone (NORFLURAZON); 4-(di-n-propylamino)-3,5-dinitrobenzenesulphonamide (ORYZALIN); 2- chloro-4-trifluoromethyl-phenyl 3-ethoxy-4-nitro-phenyl ether (OXYFLUORFEN); N-(1-ethylpropyl)-3,4-dimethyl-2,6-dinitroaniline (PENDIMETHALIN); α-chloro-2',6'-diethyl-N-(2-propoxyethyl)-acetanilide (PRETILACHLOR); 2-chloro-N-isopropylacetanilide (PROPACHLOR); isopropyl N-phenylcarbamate (PROPHAM); O-(6-chloro-3-phenyl-pyridazin-4-yl) S-octyl thiocarbonate (PYRIDATE); ethyl 2-[4-(6-chloroquinoxalin-2-yl-oxy)-phenoxy]-propionate (QUIZALOFOPETHYL); 2-[1-(ethoxamino)-butylidene]-5-(2-ethylthiopropyl)- 1,3-cyclohexadione (SETHOXYDIM); 2-chloro-4,6-bis-(ethylamino)-1,3,5-triazine (SIMAZINE); 2,4-bis-[N-ethylamino]-6-methylthio-1,3,5-triazine (SIMETRYNE); 4-ethylamino-2-t-butylamino-6-methylthio-s-triazine (TERBUTRYNE); methyl 3-[[[[(4-methoxy-6-methyl-1,3,5-triazin-2-yl)-amino]-carbonyl]-amino]-sulphonyl]-thiophene-2-carboxylate (THIAMETURON); S-[(4-chloro-phenyl)methyl]-N,N-diethylthiocarbonate(THIOBENCARB);S-(2,3,3-trichloroallyl) diisopropylthiocarbamate (TRIALLATE); 2,6-dinitro-4-trifluoromethyl-N,N-dipropyl-aniline (TRIFLURALIN). Surprisingly, some mixtures also show a synergistic action.

A mixture with other known active compounds, such as fungicides, insecticides, acaricides, nematicides, bird repellants, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomising or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.5 g and 1 kg of active compound per hectare of soil surface, preferably between 1 g and 500 g per ha.

The preparation and use of the active compounds according to the invention can be seen from the following examples.

PREPARATION EXAMPLES

Example 1

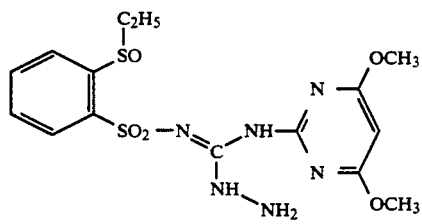

(Process (a))

A mixture of 13.3 g (0.03 mol) of N'-(4,6-dimethoxypyrimidin-2-yl)-N,'-(2-ethylsulphinyl-phenylsulphonyl)-S-methyl-isothiourea, 2 ml (0.04 mol of $N_2H_4$) of hydrazine-hydrate and 70 ml of chloroform is stirred at ° C. for 60 minutes, then dried with sodium sulphate and filtered. The filtrate is concentrated, the residue is triturated with ethanol and the product obtained in crystalline form is isolated by filtered off with suction.

9.5 g (74% of theory) of N'-(4,6-dimethoxy-pyrimidin-2-yl)-N''-amino-N'''-(2-ethylsulphinyl-phenylsulphonyl)guanidine of melting point 134° C. are obtained.

EXAMPLE 2

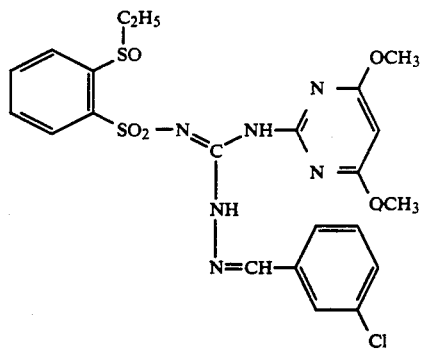

(Process (b))

A mixture of 3.4 g (8 mMol) of N'-(4,6-dimethoxy-pyrimidin-2-yl)-N''-amino-N'''-(2-ethylsulphinyl-phenylsulphonyl)-guanidine, 1.3 g (9 mMol) of 3-chloro-benzaldehyde and 40 ml of ethanol is stirred at 70° C. for 2 hours. After cooling, the product obtained in crystalline form is isolated by filtering off with suction.

4.0 g (91% of theory) of N'-(4,6-dimethoxy-pyrimidin-2-yl)-N''-(3-chloro-benzylideneamino)-N'''-(2-ethylsulphinyl-phenylsulphonyl)-guanidine of melting point 184° C. are obtained.

The compounds of the formula (I)

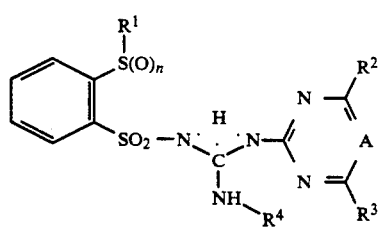

listed in Table 1 below can, for example, also be prepared analogously to Examples 1 and 2 and according to the general description of the preparation processes according to the invention.

TABLE 1

Examples of the compounds of the formula (I)

| Ex. No. | n | A | $R^1$ | $R^2$ | $R^3$ | $R^4$ | Melting point (°C.) |
|---|---|---|---|---|---|---|---|
| 3 | 1 | CH | $C_2H_5$ | $OCH_3$ | $OCH_3$ | —N=C(CH₃)₂ | 184 |
| 4 | 1 | CH | $C_2H_5$ | $OCH_3$ | $OCH_3$ | —N=CH—C₆H₅ | 187 |
| 5 | 1 | CH | $C_2H_5$ | $OCH_3$ | $OCH_3$ | —N=CH—(2-Cl-C₆H₄) | 193 |
| 6 | 1 | CH | $C_2H_5$ | $OCH_3$ | $OCH_3$ | —N=CH—(4-Cl-C₆H₄) | 208 |
| 7 | 1 | CH | $C_2H_5$ | $OCH_3$ | $OCH_3$ | —N=CH—(2-CH₃-C₆H₄) | 191 |
| 8 | 1 | CH | $C_2H_5$ | $OCH_3$ | $OCH_3$ | —N=CH—(2-OCH₃-C₆H₄) | 200 |
| 9 | 1 | CH | $C_2H_5$ | $OCH_3$ | $OCH_3$ | —N=CH—(4-CH₃-C₆H₄) | 205 |
| 10 | 1 | CH | $C_2H_5$ | $OCH_3$ | $OCH_3$ | —N=CH—(3-OCH₃-C₆H₄) | 155 |
| 11 | 1 | CH | $C_2H_5$ | $OCH_3$ | $OCH_3$ | —N=CH—(4-OCH₃-C₆H₄) | 215 |

TABLE 1-continued

Examples of the compounds of the formula (I)

| Ex. No. | n | A | R¹ | R² | R³ | R⁴ | Melting point (°C.) |
|---|---|---|---|---|---|---|---|
| 12 | 1 | CH | $C_2H_5$ | $OCH_3$ | $OCH_3$ | $-N=CH-\underset{}{\bigcirc}-N(CH_3)_2$ | 209 |
| 13 | 1 | CH | $C_3H_7$ | $OCH_3$ | $OCH_3$ | $NH_2$ | (amorphous) |
| 14 | 1 | N | $C_2H_5$ | $OCH_3$ | $OCH_3$ | $NH_2$ | 112 |
| 15 | 1 | N | $C_2H_5$ | $OCH_3$ | $OCH_3$ | $-N=CH-\underset{}{\bigcirc}$ | 166 |
| 16 | 1 | N | $C_2H_5$ | $OCH_3$ | $OCH_3$ | $-N=CH-\underset{Cl}{\bigcirc}$ | 175 |
| 17 | 1 | N | $C_2H_5$ | $OCH_3$ | $OCH_3$ | $-N=CH-\underset{Cl}{\bigcirc}$ | 204 |
| 18 | 1 | N | $C_2H_5$ | $OCH_3$ | $OCH_3$ | $-N=CH-\underset{CH_3}{\bigcirc}$ | 128 |
| 19 | 1 | N | $C_2H_5$ | $OCH_3$ | $OCH_3$ | $-N=CH-\underset{}{\bigcirc}-CH_3$ | 197 |
| 20 | 1 | N | $C_2H_5$ | $OCH_3$ | $OCH_3$ | $-N=CH-\underset{OCH_3}{\bigcirc}$ | 126 |
| 21 | 1 | N | $C_2H_5$ | $OCH_3$ | $OCH_3$ | $-N=CH-\underset{}{\bigcirc}-OCH_3$ | 189 |
| 22 | 2 | CH | $C_2H_5$ | $OCH_3$ | $OCH_3$ | $NH_2$ | 187 |
| 23 | 2 | CH | $C_2H_5$ | $OCH_3$ | $OCH_3$ | $-N=C\underset{CH_3}{\overset{CH_3}{\diagup}}$ | 209 |
| 24 | 2 | CH | $C_2H_5$ | $OCH_3$ | $OCH_3$ | $-N=CH-\underset{}{\bigcirc}$ | 221 |
| 25 | 2 | CH | $C_2H_5$ | $OCH_3$ | $OCH_3$ | $-N=CH-\underset{Cl}{\bigcirc}$ | 209 |

TABLE 1-continued

Examples of the compounds of the formula (I)

| Ex. No. | n | A | R¹ | R² | R³ | R⁴ | Melting point (°C.) |
|---|---|---|---|---|---|---|---|
| 26 | 2 | CH | $C_2H_5$ | $OCH_3$ | $OCH_3$ | —N=CH—(3-Cl-C₆H₄) | 221 |
| 27 | 2 | CH | $C_2H_5$ | $OCH_3$ | $OCH_3$ | —N=CH—(4-Cl-C₆H₄) | 229 |
| 28 | 2 | CH | $C_2H_5$ | $OCH_3$ | $OCH_3$ | —N=CH—(2-CH₃-C₆H₄) | 199 |
| 29 | 2 | CH | $C_2H_5$ | $OCH_3$ | $OCH_3$ | —N=CH—(3-CH₃-C₆H₄) | 224 |
| 30 | 2 | CH | $C_2H_5$ | $OCH_3$ | $OCH_3$ | —N=CH—(2-OCH₃-C₆H₄) | 215 |
| 31 | 2 | CH | $C_2H_5$ | $OCH_3$ | $OCH_3$ | —N=CH—(3-OCH₃-C₆H₄) | 215 |
| 32 | 2 | CH | $C_2H_5$ | $OCH_3$ | $OCH_3$ | —N=CH—C₆H₄—N(CH₃)₂ | 256 |
| 33 | 2 | N | $C_2H_5$ | $OCH_3$ | $OCH_3$ | $NH_2$ | 142 |
| 34 | 2 | N | $C_2H_5$ | $OCH_3$ | $OCH_3$ | —N=CH—C₆H₅ | 199 |
| 35 | 2 | N | $C_2H_5$ | $OCH_3$ | $OCH_3$ | —N=C(CH₃)₂ | 195 |
| 36 | 2 | N | $C_2H_5$ | $OCH_3$ | $OCH_3$ | —N=CH—(3-Cl-C₆H₄) | 201 |
| 37 | 2 | N | $C_2H_5$ | $OCH_3$ | $OCH_3$ | —N=CH—(4-Cl-C₆H₄) | 212 |

TABLE 1-continued
Examples of the compounds of the formula (I)
| Ex. No. | n | A | R¹ | R² | R³ | R⁴ | Melting point (°C.) |
|---|---|---|---|---|---|---|---|
| 38 | 2 | N | $C_2H_5$ | $OCH_3$ | $OCH_3$ | 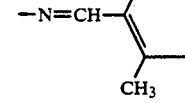 | 190 |
| 39 | 2 | N | $C_2H_5$ | $OCH_3$ | $OCH_3$ | 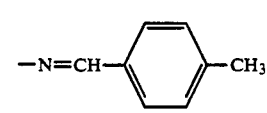 | 214 |
| 40 | 2 | N | $C_2H_5$ | $OCH_3$ | $OCH_3$ | 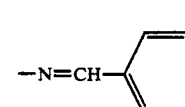 | 209 |
| 41 | 2 | N | $C_2H_5$ | $OCH_3$ | $OCH_3$ | 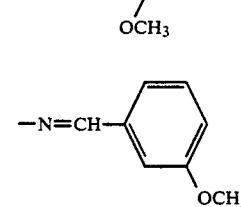 | 201 |
| 42 | 2 | N | $C_2H_5$ | $OCH_3$ | $OCH_3$ | 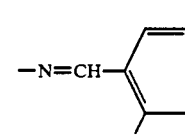 | 209 |
| 43 | 2 | N | $C_2H_5$ | $OCH_3$ | $OCH_3$ | 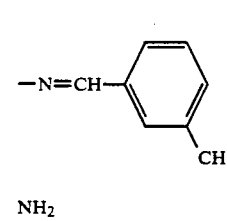 | 187 |
| 44 | 2 | N | $C_2H_5$ | $CH_3$ | $OCH_3$ | $NH_2$ | 149 |
| 45 | 2 | N | $C_2H_5$ | $CH_3$ | $OCH_3$ | 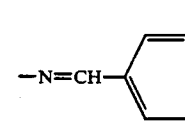 | 192 |
| 46 | 2 | N | $C_2H_5$ | $CH_3$ | $OCH_3$ | 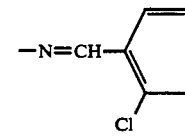 | 207 |
| 47 | 1 | N | $C_2H_5$ | $CH_3$ | $OCH_3$ | $NH_2$ | 87 |
| 48 | 1 | N | $C_2H_5$ | $CH_3$ | $OCH_3$ | 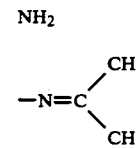 | 201 |
| 49 | 1 | N | $C_2H_5$ | $CH_3$ | $OCH_3$ | 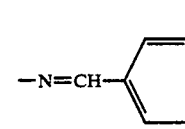 | 153 |

TABLE 1-continued

Examples of the compounds of the formula (I)

| Ex. No. | n | A | R¹ | R² | R³ | R⁴ | Melting point (°C.) |
|---|---|---|---|---|---|---|---|
| 50 | 1 | N | C₂H₅ | CH₃ | OCH₃ | 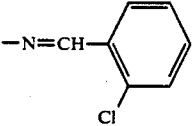 —N=CH—(2-Cl-C₆H₄) | 152 |
| 51 | 1 | N | C₂H₅ | CH₃ | OCH₃ | 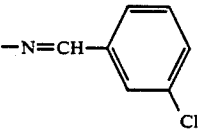 —N=CH—(3-Cl-C₆H₄) | 87 |
| 52 | 1 | N | C₂H₅ | CH₃ | OCH₃ | 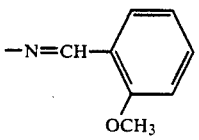 —N=CH—(2-OCH₃-C₆H₄) | 183 |
| 53 | 1 | N | C₂H₅ | CH₃ | OCH₃ | 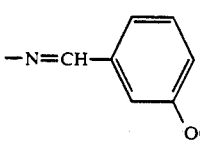 —N=CH—(3-OCH₃-C₆H₄) | 168 |
| 54 | 1 | N | C₂H₅ | CH₃ | OCH₃ | 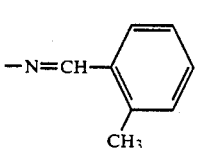 —N=CH—(2-CH₃-C₆H₄) | 173 |
| 55 | 1 | N | C₂H₅ | CH₃ | OCH₃ | 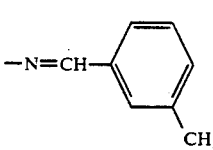 —N=CH—(3-CH₃-C₆H₄) | 157 |
| 56 | 2 | N | C₂H₅ | CH₃ | OCH₃ | 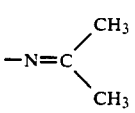 —N=C(CH₃)₂ | 215 |
| 57 | 1 | CH | C₃H₇ | OCH₃ | OCH₃ | 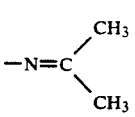 —N=C(CH₃)₂ | 169 |
| 58 | 1 | CH | C₃H₇ | OCH₃ | OCH₃ | 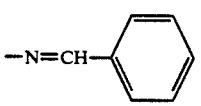 —N=CH—C₆H₅ | 155 |
| 59 | 1 | CH | C₃H₇ | OCH₃ | OCH₃ | 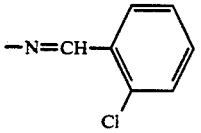 —N=CH—(2-Cl-C₆H₄) | 182 |
| 60 | 1 | CH | C₃H₇ | OCH₃ | OCH₃ | 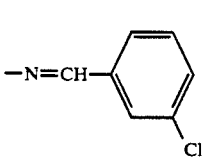 —N=CH—(3-Cl-C₆H₄) | 185 |

TABLE 1-continued

Examples of the compounds of the formula (I)

| Ex. No. | n | A | R¹ | R² | R³ | R⁴ | Melting point (°C.) |
|---|---|---|---|---|---|---|---|
| 61 | 1 | CH | $C_3H_7$ | $OCH_3$ | $OCH_3$ | $-N=CH-\text{C}_6H_4-Cl$ (p) | 185 |
| 62 | 1 | CH | $C_3H_7$ | $OCH_3$ | $OCH_3$ | $-N=CH-\text{C}_6H_4-CH_3$ (o) | 172 |
| 63 | 1 | CH | $C_3H_7$ | $OCH_3$ | $OCH_3$ | $-N=CH-\text{C}_6H_4-CH_3$ (m) | 186 |
| 64 | 1 | CH | $C_3H_7$ | $OCH_3$ | $OCH_3$ | $-N=CH-\text{C}_6H_4-CH_3$ (p) | 178 |
| 65 | 1 | CH | $C_3H_7$ | $OCH_3$ | $OCH_3$ | $-N=CH-\text{C}_6H_4-OCH_3$ (o) | 188 |
| 66 | 1 | CH | $C_3H_7$ | $OCH_3$ | $OCH_3$ | $-N=CH-\text{C}_6H_4-OCH_3$ (m) | 172 |
| 67 | 1 | CH | $C_3H_7$ | $OCH_3$ | $OCH_3$ | $-N=CH-\text{C}_6H_4-OCH_3$ (p) | 193 |
| 68 | 1 | N | $C_3H_7$ | $CH_3$ | $OCH_3$ | $NH_2$ | (amorphous) |
| 69 | 1 | N | $C_3H_7$ | $OCH_3$ | $OCH_3$ | $NH_2$ | (amorphous) |
| 70 | 2 | CH | $C_3H_7$ | $OCH_3$ | $OCH_3$ | $NH_2$ | |
| 71 | 2 | CH | $C_3H_7$ | $CH_3$ | $OCH_3$ | $NH_2$ | |
| 72 | 2 | CH | $C_2H_5$ | $CH_3$ | $OCH_3$ | $NH_2$ | |
| 73 | 2 | CH | $C_2H_5$ | H | $CH_3$ | $NH_2$ | |
| 74 | 2 | CH | $C_2H_5$ | $CH_3$ | $CH_3$ | $NH_2$ | |
| 75 | 1 | CH | $C_2H_5$ | $CH_3$ | $OCH_3$ | $NH_2$ | |
| 76 | 1 | CH | $C_2H_5$ | $CH_3$ | $CH_3$ | $NH_2$ | 126 |
| 77 | 1 | CH | $C_2H_5$ | $CH_3$ | H | $NH_2$ | 125 |
| 78 | 2 | N | $C_3H_7$ | $CH_3$ | $OCH_3$ | $NH_2$ | |
| 79 | 2 | CH | $C_3H_7$ | $CH_3$ | $CH_3$ | $NH_2$ | |
| 80 | 2 | CH | $C_3H_7$ | H | $CH_3$ | $NH_2$ | |
| 81 | 1 | CH | $C_3H_7$ | $CH_3$ | $OCH_3$ | $NH_2$ | |
| 82 | 1 | CH | $C_3H_7$ | $CH_3$ | $CH_3$ | $NH_2$ | |
| 83 | 1 | CH | $C_3H_7$ | H | $CH_3$ | $NH_2$ | 86 |
| 84 | 1 | CH | $CH(CH_3)_2$ | $OCH_3$ | $OCH_3$ | $NH_2$ | |
| 85 | 1 | N | $CH(CH_3)_2$ | $OCH_3$ | $OCH_3$ | $NH_2$ | |
| 86 | 1 | N | $CH(CH_3)_2$ | $CH_3$ | $OCH_3$ | $NH_2$ | |
| 87 | 1 | CH | $CH(CH_3)_2$ | $CH_3$ | $OCH_3$ | $NH_2$ | |
| 88 | 1 | CH | $CH(CH_3)_2$ | $CH_3$ | $CH_3$ | $NH_2$ | |
| 89 | 2 | CH | $CH(CH_3)_2$ | $OCH_3$ | $OCH_3$ | $NH_2$ | |
| 90 | 2 | CH | $CH(CH_3)_2$ | $CH_3$ | $OCH_3$ | $NH_2$ | |
| 91 | 2 | CH | $CH(CH_3)_2$ | $CH_3$ | $CH_3$ | $NH_2$ | |
| 92 | 2 | CH | $CH(CH_3)_2$ | $CH_3$ | H | $NH_2$ | |
| 93 | 2 | N | $CH(CH_3)_2$ | $OCH_3$ | $OCH_3$ | $NH_2$ | |
| 94 | 2 | N | $CH(CH_3)_2$ | $CH_3$ | $OCH_3$ | $NH_2$ | |
| 95 | 2 | N | $CH(CH_3)_2$ | $CH_3$ | $CH_3$ | $NH_2$ | |

TABLE 1-continued

Examples of the compounds of the formula (I)

| Ex. No. | n | A | $R^1$ | $R^2$ | $R^3$ | $R^4$ | Melting point (°C.) |
|---|---|---|---|---|---|---|---|
| 96 | 1 | N | $C_3H_7$ | $OCH_3$ | $OCH_3$ | $-N=CH-C_6H_5$ | 118 |
| 97 | 1 | N | $C_3H_7$ | $OCH_3$ | $OCH_3$ | $-N=CH-C_6H_4-CH_3$ | |
| 98 | 1 | N | $C_3H_7$ | $OCH_3$ | $OCH_3$ | $-N=CH-C_6H_4-Cl$ (ortho) | |
| 99 | 1 | N | $C_3H_7$ | $OCH_3$ | $OCH_3$ | $-N=CH-C_6H_4-CN$ | |
| 100 | 1 | N | $C_3H_7$ | $OCH_3$ | $OCH_3$ | $-N=CH-C_6H_4-NO_2$ | |
| 101 | 1 | N | $C_3H_7$ | $CH_3$ | $OCH_3$ | $-N=CH-C_6H_5$ | 169 |
| 102 | 1 | N | $C_3H_7$ | $CH_3$ | $OCH_3$ | $-N=CH-C_6H_4-SCH_3$ | |
| 103 | 1 | N | $C_3H_7$ | $CH_3$ | $OCH_3$ | $-N=CH-C_6H_4-COOH$ | |
| 104 | 1 | N | $C_3H_7$ | $CH_3$ | $OCH_3$ | $-N=CH-C_6H_4-F$ | |
| 105 | 1 | N | $C_3H_7$ | $CH_3$ | $OCH_3$ | $-N=CH-C_6H_4-CF_3$ | |
| 106 | 1 | CH | $C_3H_7$ | $CH_3$ | $CH_3$ | $-N=CH-C_6H_5$ | |

TABLE 1-continued

Examples of the compounds of the formula (I)

| Ex. No. | n | A | R$^1$ | R$^2$ | R$^3$ | R$^4$ | Melting point (°C.) |
|---|---|---|---|---|---|---|---|
| 107 | 1 | CH | C$_3$H$_7$ | CH$_3$ | OCH$_3$ | —N=CH—C$_6$H$_5$ | |
| 108 | 1 | CH | C$_3$H$_7$ | H | CH$_3$ | —N=CH—C$_6$H$_5$ | 135 |
| 109 | 2 | CH | C$_3$H$_7$ | OCH$_3$ | OCH$_3$ | —N=CH—C$_6$H$_5$ | |
| 110 | 2 | CH | C$_3$H$_7$ | OCH$_3$ | OCH$_3$ | —N=CH—C$_6$H$_4$—Br | |
| 111 | 2 | CH | C$_3$H$_7$ | OCH$_3$ | OCH$_3$ | —N=CH—C$_6$H$_4$—CH$_3$ | |
| 112 | 2 | N | C$_3$H$_7$ | OCH$_3$ | CH$_3$ | —N=CH—C$_6$H$_5$ | |
| 113 | 2 | N | C$_3$H$_7$ | CH$_3$ | OCH$_3$ | —N=CH—C$_6$H$_4$—Cl | |
| 114 | 2 | N | C$_3$H$_7$ | OCH$_3$ | OCH$_3$ | —N=CH—C$_6$H$_5$ | |
| 115 | 2 | N | C$_3$H$_7$ | OCH$_3$ | OCH$_3$ | —N=CH—C$_6$H$_4$—CH$_3$ | |
| 116 | 2 | N | C$_3$H$_7$ | OCH$_3$ | OCH$_3$ | —N=CH—C$_6$H$_4$—Cl | |
| 117 | 2 | CH | C$_3$H$_7$ | CH$_3$ | CH$_3$ | —N=CH—C$_6$H$_5$ | |
| 118 | 2 | CH | C$_3$H$_7$ | CH$_3$ | OCH$_3$ | —N=CH—C$_6$H$_5$ | |

TABLE 1-continued
Examples of the compounds of the formula (I)
| Ex. No. | n | A | $R^1$ | $R^2$ | $R^3$ | $R^4$ | Melting point (°C.) |
|---|---|---|---|---|---|---|---|
| 119 | 2 | CH | $C_3H_7$ | H | $CH_3$ | 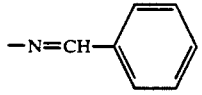 | |
| 120 | 1 | CH | $CH(CH_3)_2$ | $OCH_3$ | $OCH_3$ | 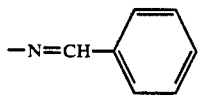 | |
| 121 | 1 | CH | $CH(CH_3)_2$ | $CH_3$ | $OCH_3$ | 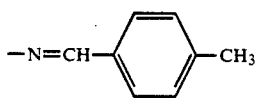 | |
| 122 | 1 | CH | $CH(CH_3)_2$ | H | $CH_3$ | 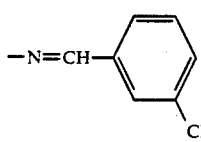 | |
| 123 | 1 | N | $CH(CH_3)_2$ | $CH_3$ | $OCH_3$ | 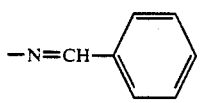 | |
| 124 | 1 | N | $CH(CH_3)_2$ | $OCH_3$ | $OCH_3$ | 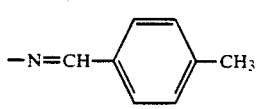 | |
| 125 | 1 | CH | $CH(CH_3)_2$ | $CH_3$ | $CH_3$ | 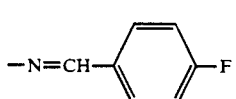 | |
| 126 | 2 | CH | $CH(CH_3)_2$ | $CH_3$ | $OCH_3$ | 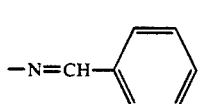 | |
| 127 | 2 | CH | $CH(CH_3)_2$ | $OCH_3$ | $OCH_3$ | 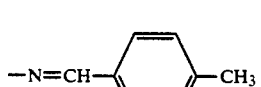 | |
| 128 | 2 | CH | $CH(CH_3)_2$ | H | $CH_3$ | 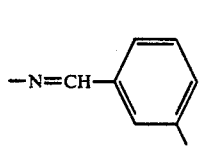 | |
| 129 | 2 | CH | $CH(CH_3)_2$ | $CH_3$ | $CH_3$ | 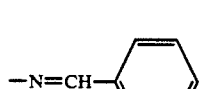 | |
| 130 | 2 | N | $CH(CH_3)_2$ | $CH_3$ | $OCH_3$ | 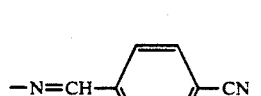 | |

TABLE 1-continued

Examples of the compounds of the formula (I)

| Ex. No. | n | A | R¹ | R² | R³ | R⁴ | Melting point (°C.) |
|---|---|---|---|---|---|---|---|
| 131 | 2 | N | CH(CH₃)₂ | OCH₃ | OCH₃ | −N=CH−C₆H₄−COOH | |
| 132 | 1 | CH | C₂H₅ | CH₃ | OCH₃ | −N=CH−C₆H₄−F | |
| 133 | 1 | CH | C₂H₅ | H | CH₃ | −N=CH−C₆H₅ | 203 |
| 134 | 2 | CH | C₂H₅ | CH₃ | OCH₃ | −N=CH−C₆H₄−Br | |
| 135 | 2 | CH | C₂H₅ | H | CH₃ | −N=CH−C₆H₄−CH₃ | |
| 136 | 1 | CH | C₂H₅ | CH₃ | CH₃ | −N=CH−C₆H₅ | 210 |
| 137 | 1 | N | C₃H₇ | CH₃ | OCH₃ | −N=C(CH₃)₂ | 162 |
| 138 | 1 | CH | C₂H₅ | H | CH₃ | −N=CH−C₆H₄−Cl | 207 |
| 139 | 1 | CH | C₂H₅ | H | CH₃ | −N=CH−C₆H₄−CH₃ | 185 |
| 140 | 1 | CH | C₂H₅ | H | CH₃ | −N=CH−C₆H₃−Cl,Cl | 205 |
| 141 | 1 | CH | C₃H₇ | H | CH₃ | −N=CH−C₆H₄−Cl | 215 |
| 142 | 1 | CH | C₃H₇ | H | CH₃ | −N=CH−C₆H₄−CH₃ | 203 |

TABLE 1-continued

Examples of the compounds of the formula (I)

| Ex. No. | n | A | R¹ | R² | R³ | R⁴ | Melting point (°C.) |
|---|---|---|---|---|---|---|---|
| 143 | 1 | CH | $C_3H_7$ | H | $CH_3$ | $-N=CH-\text{(2,4-dichlorophenyl)}$ | 180 |
| 144 | 1 | N | $C_3H_7$ | $OCH_3$ | $OCH_3$ | $-N=C(CH_3)_2$ | 153 |

Starting substances of the formula (II)

Example (II-1)

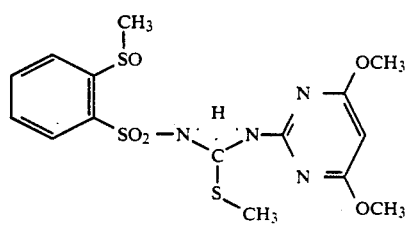

20.7 g (0.05 mol) of N'-(4,6-dimethoxy-pyrimidin-2-yl)-N''-(2-methylthio-phenylsulphonyl)-S-methyl-isothiourea are stirred with 100 ml of acetic acid and 6.8 g of a 30% strength aqueous solution of hydrogen peroxide (0.06 mol of $H_2O_2$) are added dropwise to this mixture at 20° C. to 30° C. The reaction mixture is then stirred at 60° C. for 70° C. for 5 hours; the stirring is continued at 20° C. for a further 15 hours and the crystalline product is then isolated by filtering off with suction.

19.356 g (90% of theory) of N'-(4,6-dimethoxy-pyrimidin-2-yl)-N''-(2-methylsulphinyl-phenylsulphonyl)-S-methylisothiourea of melting point 117° C. are obtained.

Use Examples

The compound shown below is used as a comparison substance in the following use examples:

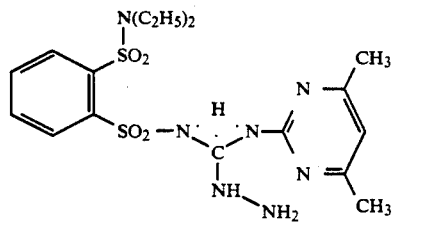 (A)

N'-(4,6-dimethyl-pyrimidin-2-yl)-N''-amino-N'''-(2-diethylaminosulphonyl-phenylsulphonyl)-guanidine (disclosed in EP-A 173,319, Ex. 40).

The formulae of the compounds according to the invention used for the use examples are—with the numbering of the preparation examples (Ex. No. from Table 1) listed individually below.

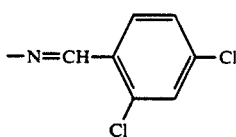 (1)

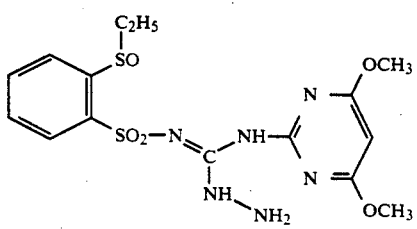 (3)

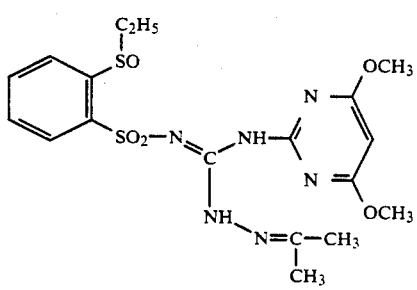 (4)

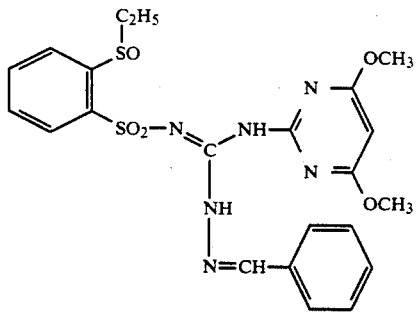 (5)

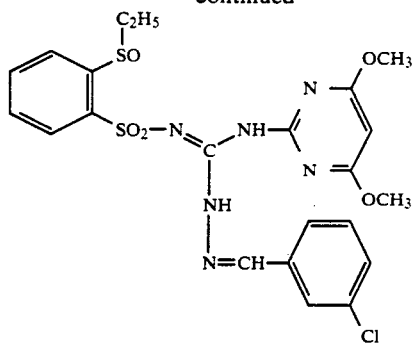
(2)
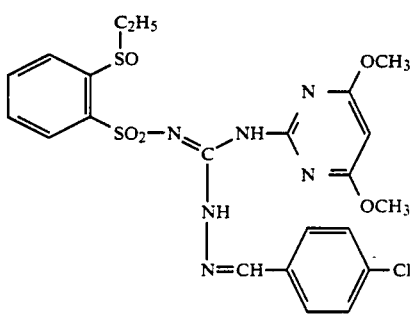
(6)
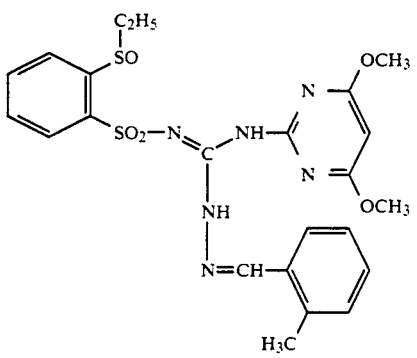
(7)
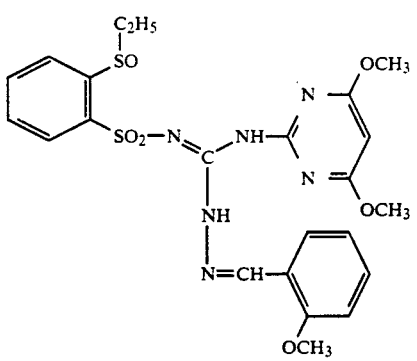
(8)
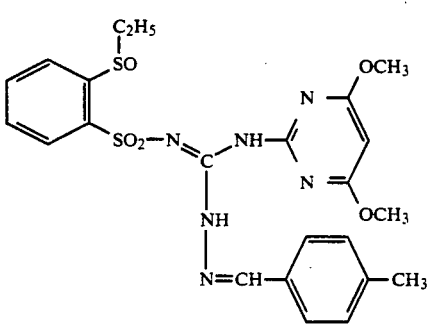
(9)
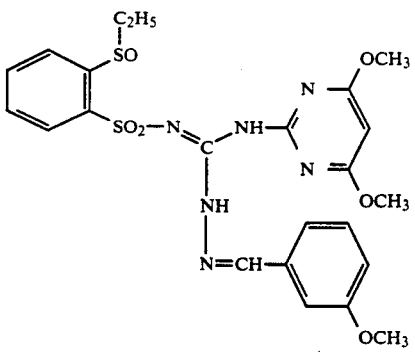
(10)
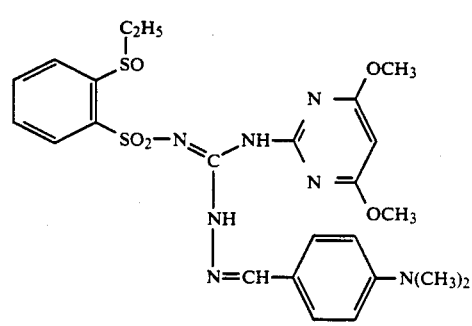
(12)
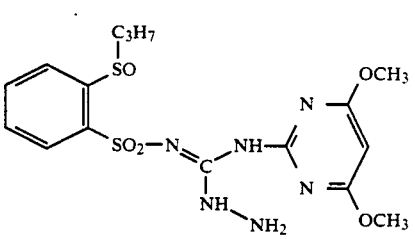
(13)
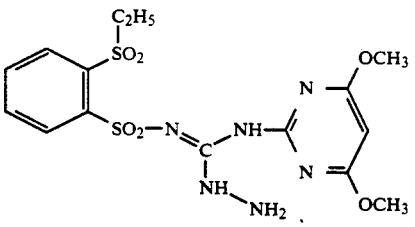
(22)
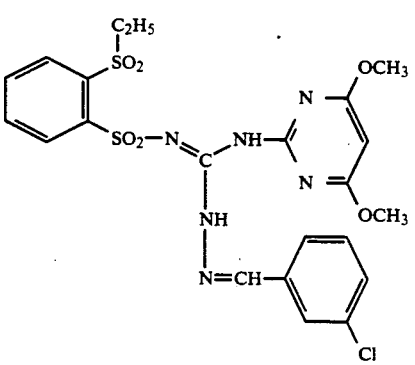
(26)

Example A

| Post-emergence test | |
|---|---|
| Solvent: | 5 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of active compound in such a way as to apply the particular amounts of active compound desired per unit area. The concentration of the spray liquor is so chosen that the particular amounts of active compound desired are applied in 1,000 l of water/ha. After three weeks, the degree of damage to the plants is rated in % damage in comparison to the development of the untreated control. The figures denote:

0% = no action (like untreated control)
100% = total destruction

In this test, for example, the compounds according to the following preparation examples: 1, 2, 3, 4, 5, 6, 7, 8, 9, 10, 11, 12, 13, 22, 26, 35, 39 and 42 show a clearly superior activity compared to the prior art together with good tolerability for crop plants, such as, for example, corn (maize) and wheat.

Example B

| Pre-emergence test | |
|---|---|
| Solvent: | 5 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, for example, the compounds according to the following preparation examples: 1 and 22, show a clearly superior activity compared to the prior art together with good tolerability for crop plants, such as, for example, wheat, soya and cotton.

It will be understood that the specification and examples are illustrative but not limitative of the present invention and that other embodiments within the spirit and scope of the invention will suggest themselves to those skilled in the art.

We claim:

1. A sulphonylguanidinoazine having the formula $R^1$ to $R^4$ are the groups defined herein, n represents the numbers 1 or 2, A represents a C-X group, where X represents hydrogen, fluorine or chlorine, $R^1$ represents $C_2$–$C_6$-alkyl, $R^2$ and $R^3$ are identical or different and represent hydrogen, fluorine, chlorine, bromine, $C_1$–$C_4$-alkyl, $C_1$–$C_4$-alkoxy, $C_1$–$C_4$-halogenoalkoxy, $C_1$–$C_4$-alkylthio, $C_1$–$C_4$-alkylamino or di-($C_1$–$C_2$-alkyl)amino, and $R^4$ represents amino or the group $$-N=C\begin{matrix}R^5\\R^6\end{matrix},$$

in which $R^5$ represents hydrogen, $C_1$–$C_5$-alkyl which is optionally substituted by fluorine, chlorine and/or bromine, or phenyl or benzyl which are in each case optionally substituted by fluorine, chlorine, bromine, $C_1$–$C_4$ alkyl and/or $C_1$–$C_4$-alkoxy, $R^6$ represents hydrogen, $C_1$–$C_{20}$-alkyl, $C_2$–$C_{10}$-alkenyl, $C_2$–$C_{10}$-alkinyl or $C_4$–$C_{10}$-alkadienyl which are in each case optionally substituted by fluorine, chlorine and/or bromine, $C_1$–$C_4$-alkoxy-$C_1$–$C_4$-alkyl, $C_1$–$C_4$-alkylthio-$C_1$–$C_4$-alkyl, phenyl which is optionally substituted by fluorine, chlorine, bromine, carboxyl, cyano, nitro, amino, $C_1$–$C_4$-alkyl (which is optionally substituted by fluorine and/or chlorine), $C_1$–$C_4$-alkoxy (which is optionally substituted by fluorine and/or chlorine), $C_1$–$C_4$-alkylthio (which is optionally substituted by fluorine and/or chlorine), di-($C_1$–$C_4$-alkyl)-amino, $C_1$–$C_4$-alkoxy-carbonyl and/or phenoxy (which is optionally substituted by fluorine, chlorine and/or trifluoromethyl), or naphthyl, or represents pyridyl, pyrrolyl, furyl, thiazolyl or thienyl which are in each case optionally substituted by cyano, nitro, fluorine, chlorine, bromine, $C_1$–$C_4$-alkyl and/or $C_1$–$C_4$-alkoxy, or represents dithienyl, or phenyl-$C_1$–$C_2$-alkyl or phenylethenyl which are in each case- optionally substituted by fluorine, chlorine, bromine, $C_1$–$C_4$-alkyl and/or $C_1$–$C_6$-alkoxy, or represents $C_1$–$C_5$-alkoxy, $C_1$–$C_6$-alkoxy-carbonyl or di-($C_1$–$C_4$-alkyl)amino, or together with $R^5$ represents $C_2$–$C_6$-alkanediyl which is optionally substituted by fluorine, chlorine, bromine, $C_1$–$C_4$-alkyl and/or $C_1$–$C_4$-alkoxycarbonyl.

2. A sulphonylguanidinoazine according to claim 1, in which n represents the numbers 1 or 2, A represents a CH group, $R^1$ represents ethyl, propyl, isopropyl, butyl, isobutyl or sec-butyl, $R^2$ represents hydrogen, chlorine, methyl, ethyl, trifluoromethyl, methoxymethyl, methoxy, ethoxy, difluoromethoxy, methylthio, methylamino, ethylamino or dimethylamino, $R^3$ represents hydrogen, chlorine, methyl, ethyl, trifluoromethyl, methoxy, ethoxy, difluoromethoxy, methylthio, methylamino, ethylamino or dimethylamino, and $R^4$ represents amino or the group

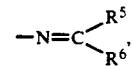

in which $R^5$ represents hydrogen, $C_1$–$C_4$-alkyl or phenyl, $R^6$ represents $C_1$–$C_{10}$-alkyl, $C_2$–$C_{10}$-alkenyl or $C_4$–$C_{10}$-alkadienyl, phenyl which is optionally substituted by fluorine, chlorine, bromine, carboxyl, cyano, nitro, methyl, ethyl, trifluoromethyl-, methoxy, ethoxy, difluoromethoxy, trifluoromethoxy, methylthio, ethylthio, difluoromethylthio, trifluoromethylthio, dimethylamino and/or phenoxy (which is optionally substituted by fluorine, chlorine and/or trifluoromethyl), pyridyl, furyl, thiazolyl or thienyl which are in each case optionally substituted by cyano, nitro, fluorine, chlorine, bromine, methyl, ethyl, methoxy or ethoxy, or represents dithienyl, benzyl or phenylethenyl, $C_1$–$C_4$-alkoxy, $C_1$–$C_4$-alkoxycarbonyl or dimethylamino, or together with $R^5$ represents butane-1,4-diyl (tetramethylene) or pentane-1,5-diyl (pentamethylene).

3. A herbicidal composition comprising a herbicidally effective amount of a compound according to claim 1 and a diluent.

4. A method of combating unwanted vegetation which comprises applying to such vegetation or to a locus from which it is desired to exclude such vegetation a herbicidally effective amount of a compound according to claim 1.

* * * * *

UNITED STATES PATENT AND TRADEMARK OFFICE
CERTIFICATE OF CORRECTION

PATENT NO. : 5,217,522

DATED : June 8, 1993

INVENTOR(S) : Riebel, et al.

It is certified that error appears in the above-identified patent and that said Letters Patent is hereby corrected as shown below:

| | |
|---|---|
| Title Page | ABSTRACT: Last line after " halogen " insert -- $R^1$ to $R^4$ are the groups defined herein -- |
| Col. 4, lines 3-4 | Delete " $C_1$-$C_6$-alkoxy " and substitute -- $C_1$-$C_4$-alkoxy -- |
| Col. 38, lines 39-40 | After " formula " delete " $R^1$ to $R^4$ are the groups defined herein " and substitute 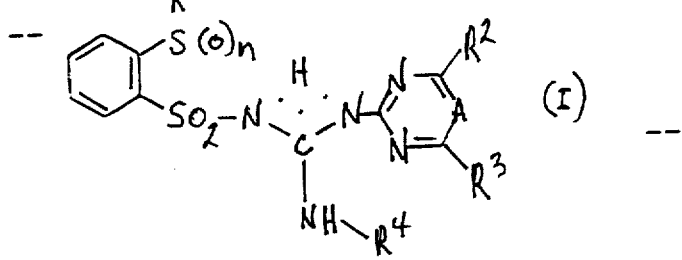 -- |
| Col. 38, line 47 | After " alkyl," insert -- $C_1$-$C_4$-halogenoalkyl, $C_1$-$C_2$-alkoxy-$C_1$-$C_2$-alkyl, -- |

UNITED STATES PATENT AND TRADEMARK OFFICE
CERTIFICATE OF CORRECTION

PATENT NO. : 5,217,522

DATED : June 8, 1993

INVENTOR(S) : Riebel, et al.

It is certified that error appears in the above-identified patent and that said Letters Patent is hereby corrected as shown below:

Col. 39, line 15  Delete " $C_1$-$C_6$-alkoxy " and substitute -- $C_1$-$C_4$-alkoxy --

Col. 39, line 16  Delete " $C_1$-$C_5$-alkoxy " and substitute -- $C_1$-$C_6$-alkoxy --

Signed and Sealed this

Twenty-fifth Day of October, 1994

*Attest:*

BRUCE LEHMAN

*Attesting Officer*    *Commissioner of Patents and Trademarks*